United States Patent
Eskridge

(10) Patent No.: US 9,848,906 B1
(45) Date of Patent: Dec. 26, 2017

(54) STENT RETRIEVER HAVING AN EXPANDABLE FRAGMENT GUARD

(71) Applicant: Joe Michael Eskridge, Clyde Hill, WA (US)

(72) Inventor: Joe Michael Eskridge, Clyde Hill, WA (US)

( * ) Notice: Subject to any disclaimer, the term of this patent is extended or adjusted under 35 U.S.C. 154(b) by 0 days.

(21) Appl. No.: 15/627,806

(22) Filed: Jun. 20, 2017

(51) Int. Cl.
- *A61B 17/22* (2006.01)
- *A61B 17/3207* (2006.01)
- *A61F 2/95* (2013.01)
- *A61F 2/86* (2013.01)
- *A61B 17/221* (2006.01)
- *A61F 2/01* (2006.01)

(52) U.S. Cl.
CPC .... *A61B 17/320725* (2013.01); *A61B 17/221* (2013.01); *A61F 2/013* (2013.01); *A61F 2/86* (2013.01); *A61F 2/95* (2013.01); *A61B 2017/22081* (2013.01); *A61B 2017/320741* (2013.01); *A61F 2002/011* (2013.01); *A61F 2002/016* (2013.01); *A61F 2002/9511* (2013.01); *A61F 2002/9528* (2013.01)

(58) Field of Classification Search
CPC .......... A61B 17/221; A61B 2017/2212; A61B 2017/2215; A61B 2017/2217; A61B 2017/22081; A61B 2017/320008; A61B 2017/320056; A61B 17/320725; A61B 2017/320741; A61F 2/013; A61F 2002/015; A61F 2002/016; A61F 2/01; A61F 2002/011; A61F 2002/018
See application file for complete search history.

(56) References Cited

U.S. PATENT DOCUMENTS

| | | | |
|---|---|---|---|
| 4,762,129 | A | 8/1988 | Bonzel |
| 4,794,931 | A | 1/1989 | Yock |
| 4,932,413 | A | 6/1990 | Sbockey |
| 5,160,321 | A | 11/1992 | Sahota |
| 5,254,088 | A | 10/1993 | Lundquist et al. |
| 5,509,900 | A | 4/1996 | Kirkman |
| 5,571,173 | A | 11/1996 | Parodi |

(Continued)

FOREIGN PATENT DOCUMENTS

| | | |
|---|---|---|
| EP | 1645242 A2 | 4/2006 |
| EP | 1955661 | 8/2008 |

(Continued)

OTHER PUBLICATIONS

Machi Paolo et al. Solitaire FR thrombectomy system: immediate results in 56 1-22 consecutive acute ischemic troke patients. J Neurointervent Surg 2012; 4(1):pp. 62-66, procedure, fig. 1,2.

*Primary Examiner* — Jonathan Miles
(74) *Attorney, Agent, or Firm* — Timothy E. Siegel Patent Law, PLLC; Timothy E. Siegel

(57) ABSTRACT

A stent retriever assembly having a proximal end and a distal end, and including a mesh tube having a distal and proximal end, and being connected to a first wire. Also, a blood-porous fragment guard is at the distal end of the mesh tube, the fragment guard including spokes joined at a central hub and extending radially and proximally from the central hub, and wherein a second wire is connected to the central hub so that when the second wire is pulled proximally relative to the first wire, the hub is pulled proximally, causing the spokes to spread out and causing the fragment guard to widen.

14 Claims, 3 Drawing Sheets

(56) References Cited

U.S. PATENT DOCUMENTS

| | | | |
|---|---|---|---|
| 5,735,289 A | 4/1998 | Pfeffer et al. | |
| 6,010,517 A | 1/2000 | Baccaro | |
| 6,059,822 A | 5/2000 | Kanesaka et al. | |
| 6,142,987 A * | 11/2000 | Tsugita | A61F 2/01 604/500 |
| 6,283,991 B1 | 9/2001 | Cox et al. | |
| 6,309,399 B1 | 10/2001 | Barbut | |
| 6,344,041 B1 | 2/2002 | Kupiecki et al. | |
| 6,371,972 B1 | 4/2002 | Wallace et al. | |
| 6,391,044 B1 | 5/2002 | Yadav et al. | |
| 6,540,722 B1 * | 4/2003 | Boyle | A61F 2/013 604/104 |
| 6,558,405 B1 * | 5/2003 | McInnes | A61F 2/013 606/200 |
| 6,652,556 B1 | 11/2003 | Van Tassel et al. | |
| 6,695,813 B1 * | 2/2004 | Boyle | A61F 2/013 604/106 |
| 6,712,766 B2 | 3/2004 | Harada | |
| 6,716,237 B1 * | 4/2004 | Alt | A61F 2/013 606/108 |
| 7,160,318 B2 | 1/2007 | Greenberg et al. | |
| 7,195,636 B2 | 3/2007 | Avellanet et al. | |
| 7,226,475 B2 | 6/2007 | Lenz et al. | |
| 7,621,928 B2 | 11/2009 | Thramann et al. | |
| 7,662,168 B2 | 2/2010 | McGuckin et al. | |
| 7,927,350 B2 | 4/2011 | Rabbitte | |
| 8,123,796 B2 | 2/2012 | Kasprzak | |
| 8,512,399 B2 | 8/2013 | Lafontaine | |
| 8,529,614 B2 | 9/2013 | Berez | |
| 8,545,530 B2 | 10/2013 | Eskridge | |
| 8,551,132 B2 | 10/2013 | Eskridge et al. | |
| 8,556,930 B2 | 10/2013 | Ellingwood | |
| 8,668,729 B2 | 3/2014 | Kaufmann et al. | |
| 8,734,504 B2 | 5/2014 | Kelly | |
| 8,753,362 B2 | 6/2014 | Widomski et al. | |
| 8,876,863 B2 | 11/2014 | Eskridge | |
| 8,911,490 B2 | 12/2014 | Perkins | |
| 2002/0004667 A1 * | 1/2002 | Adams | A61F 2/013 606/200 |
| 2002/0013616 A1 | 1/2002 | Carter et al. | |
| 2002/0022858 A1 * | 2/2002 | Demond | A61F 2/01 606/200 |
| 2002/0026211 A1 * | 2/2002 | Khosravi | A61F 2/01 606/200 |
| 2002/0042626 A1 * | 4/2002 | Hanson | A61F 2/013 606/200 |
| 2002/0072730 A1 | 6/2002 | McGill et al. | |
| 2002/0103501 A1 * | 8/2002 | Diaz | A61F 2/01 606/200 |
| 2002/0107534 A1 | 8/2002 | Schaefer et al. | |
| 2002/0138133 A1 | 9/2002 | Lenz et al. | |
| 2002/0165576 A1 * | 11/2002 | Boyle | A61B 17/221 606/200 |
| 2002/0165601 A1 | 11/2002 | Clerc | |
| 2003/0109917 A1 | 6/2003 | Rudin | |
| 2004/0034386 A1 | 2/2004 | Fulton et al. | |
| 2004/0122466 A1 * | 6/2004 | Bales | A61F 2/013 606/200 |
| 2004/0199197 A1 | 10/2004 | Eidenschink et al. | |
| 2005/0038460 A1 | 2/2005 | Jayaraman | |
| 2005/0060017 A1 | 3/2005 | Fischell et al. | |
| 2005/0096735 A1 | 5/2005 | Hojeibane et al. | |
| 2005/0283182 A1 | 12/2005 | Pierce et al. | |
| 2006/0058834 A1 | 3/2006 | Do et al. | |
| 2006/0106421 A1 | 5/2006 | Teoh | |
| 2006/0135943 A1 | 6/2006 | Mandrusov et al. | |
| 2006/0224179 A1 | 10/2006 | Kucharczyk et al. | |
| 2006/0264905 A1 | 11/2006 | Eskridge et al. | |
| 2006/0271154 A1 | 11/2006 | Woodall | |
| 2006/0287668 A1 * | 12/2006 | Fawzi | A61F 2/013 606/200 |
| 2007/0088387 A1 | 4/2007 | Eskridge et al. | |
| 2007/0191884 A1 | 8/2007 | Eskridge et al. | |
| 2007/0299461 A1 | 12/2007 | Elliott | |
| 2008/0004687 A1 | 1/2008 | Barbut et al. | |
| 2008/0039929 A1 | 2/2008 | Davis et al. | |
| 2008/0140051 A1 * | 6/2008 | Bei | A61F 2/013 604/509 |
| 2008/0243170 A1 | 10/2008 | Jenson et al. | |
| 2009/0024157 A1 | 1/2009 | Anukhin | |
| 2009/0082803 A1 | 3/2009 | Adams et al. | |
| 2009/0132024 A1 | 5/2009 | Berkhoff | |
| 2009/0171274 A1 | 7/2009 | Harlev et al. | |
| 2009/0192405 A1 | 7/2009 | Carney | |
| 2009/0292307 A1 | 11/2009 | Razack | |
| 2009/0326640 A1 | 12/2009 | Yoshimura et al. | |
| 2010/0042201 A1 | 2/2010 | Sherif | |
| 2010/0057019 A1 | 3/2010 | Zelenka | |
| 2010/0087850 A1 * | 4/2010 | Razack | A61B 17/221 606/200 |
| 2010/0087908 A1 * | 4/2010 | Hilaire | A61F 2/013 623/1.11 |
| 2010/0234878 A1 | 9/2010 | Hruska et al. | |
| 2010/0280534 A1 | 11/2010 | Sher | |
| 2011/0040314 A1 | 2/2011 | McGuckin, Jr. et al. | |
| 2011/0040319 A1 * | 2/2011 | Fulton, III | A61B 17/22 606/194 |
| 2011/0046669 A1 | 2/2011 | Goraltchouk et al. | |
| 2011/0112614 A1 | 5/2011 | Haarer | |
| 2011/0118769 A1 | 5/2011 | Bliss et al. | |
| 2011/0125181 A1 | 5/2011 | Brady | |
| 2011/0137334 A1 | 6/2011 | Anderson et al. | |
| 2011/0160833 A1 | 6/2011 | Gonzalez et al. | |
| 2011/0190863 A1 * | 8/2011 | Ostroot | A61F 2/013 623/1.11 |
| 2011/0196414 A1 * | 8/2011 | Porter | A61B 17/221 606/200 |
| 2012/0046676 A1 | 2/2012 | Morsi | |
| 2012/0053596 A1 | 3/2012 | Gordon | |
| 2012/0071911 A1 | 3/2012 | Sadasivan et al. | |
| 2012/0130408 A1 | 5/2012 | Schur et al. | |
| 2013/0090682 A1 | 4/2013 | Bachman et al. | |
| 2013/0197567 A1 * | 8/2013 | Brady | A61B 17/221 606/200 |
| 2013/0204290 A1 | 8/2013 | Clarke et al. | |
| 2013/0345738 A1 | 12/2013 | Eskridge | |
| 2014/0005651 A1 | 1/2014 | Eskridge | |
| 2014/0074149 A1 | 3/2014 | Garcia et al. | |
| 2014/0094896 A1 | 4/2014 | Berez et al. | |
| 2014/0114342 A1 | 4/2014 | Berez et al. | |
| 2014/0121672 A1 * | 5/2014 | Folk | A61F 2/013 606/127 |
| 2014/0172071 A1 | 6/2014 | Berez et al. | |
| 2015/0313732 A1 * | 11/2015 | Fulton, III | A61B 17/22 623/1.11 |
| 2016/0120570 A1 * | 5/2016 | Kobayashi | A61B 19/54 606/166 |
| 2016/0206426 A1 * | 7/2016 | Khoynezhad | A61B 17/221 |
| 2017/0112514 A1 * | 4/2017 | Marchand | A61B 17/221 |
| 2017/0119408 A1 * | 5/2017 | Ma | A61B 17/221 |
| 2017/0128089 A1 * | 5/2017 | Ma | A61B 17/221 |

FOREIGN PATENT DOCUMENTS

| | | |
|---|---|---|
| EP | 2308383 B1 | 6/2014 |
| RU | 2407466 C1 | 12/2010 |
| WO | 9000371 | 1/1990 |
| WO | 9825656 | 6/1998 |
| WO | 0128434 A1 | 4/2001 |
| WO | 0135839 A2 | 5/2001 |
| WO | 03099168 A2 | 12/2003 |
| WO | 2005037129 A1 | 4/2005 |
| WO | 2012167156 A1 | 12/2012 |
| WO | 2013109784 A1 | 7/2013 |

* cited by examiner

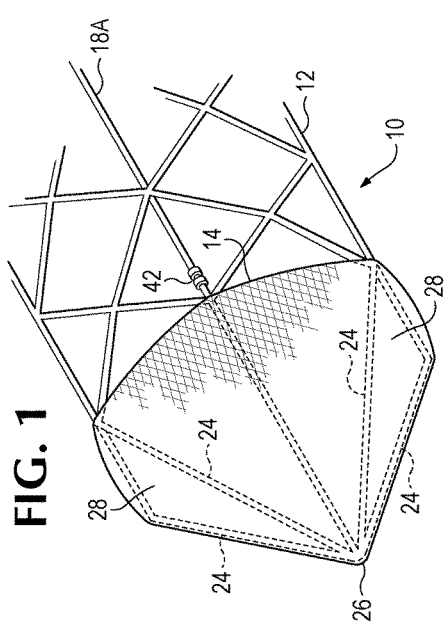
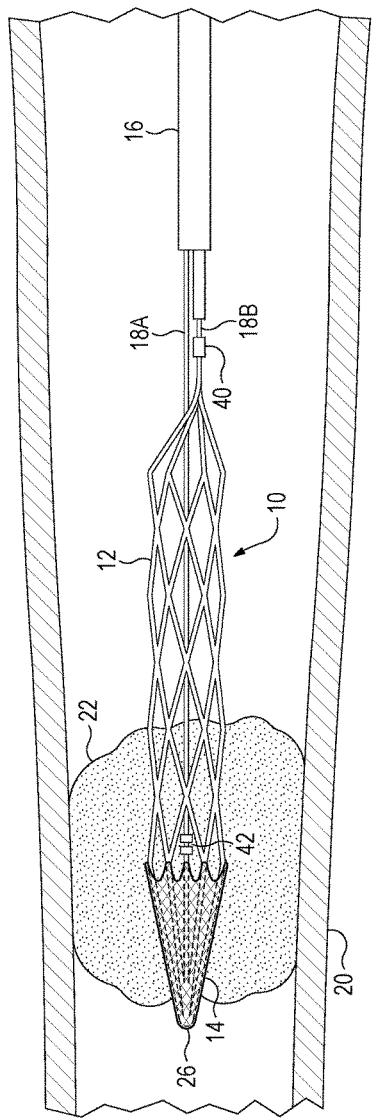
FIG. 1
FIG. 2

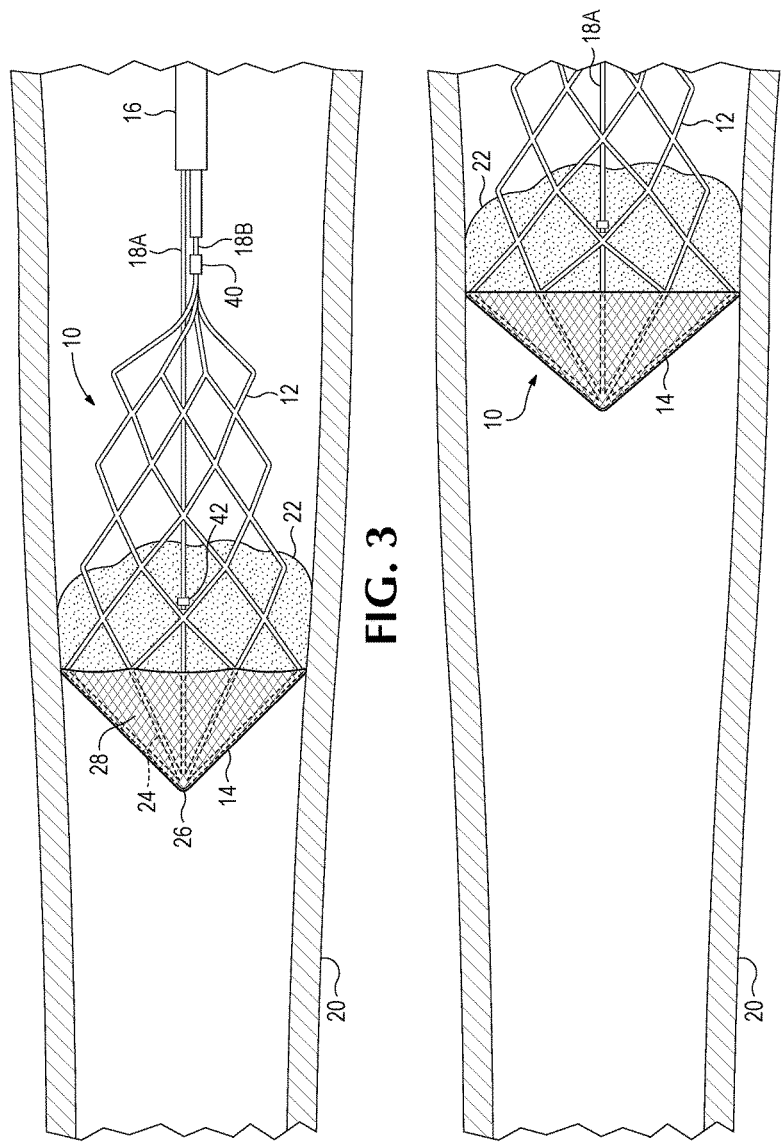

STENT RETRIEVER HAVING AN
// EXPANDABLE FRAGMENT GUARD

BACKGROUND

The medical arts have advanced rapidly in the area of stroke treatment. Until recently, only medicinal treatment could be offered. Then, stents capable of retrieving the clot material blocking a blood vessel in an ischemic stroke were developed. Now, if a patient is seen quickly after onset the clot material can be swiftly removed, thereby saving a great deal of brain function, that would otherwise be lost.

Still, many challenges remain, in the removal of a clot that blocks a cerebral artery. One of these challenges is the tendency of fragments of material to break off of the clot as it is being removed, flow in the direction of blood flow, and lodge anew in some narrow cerebral artery, causing a secondary stroke, which can be damaging.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a stent retriever assembly having a proximal end and a distal end, and including a mesh tube having a distal and proximal end, and being connected to a first wire. Also, a blood-porous fragment guard is at the distal end of the mesh tube, the fragment guard including spokes joined at a central hub and extending radially and proximally from the central hub, and wherein a second wire is connected to the central hub so that when the second wire is pulled proximally relative to the first wire, the hub is pulled proximally, causing the spokes to spread out and causing the fragment guard to widen.

In a second separate aspect, the present invention may take the form of a method of removing a clot from an artery, utilizing a stent retriever assembly having a proximal end and a distal end. The stent retriever includes a mesh tube having a distal and proximal end, and being connected to a first wire. A blood-porous fragment guard at the distal end of the mesh tube, the fragment guard including spokes joined at a central hub and extending radially and proximally from the central hub, and wherein a second wire is connected to the central hub so that when the second wire is pulled proximally relative to the first wire, the hub is pulled proximally, causing the spokes to spread out and causing the fragment guard to widen. In the method, this stent retriever is deployed to a proximal side of the clot and pushed through the clot. Then the second wire is pulled, relative to the first wire, thereby widening the fragment guard, and the stent retriever is pulled proximally to pull material from the clot proximally.

In a third separate aspect, the present invention may take the form of a stent retriever catheter assembly having a proximal end and a distal end, and including a catheter, including a flexible tube sized to fit through the arterial system of a person, and to reach a blood clot in an artery. A first and a second wire extend through the tube, and a handle is connected to the first and second wires, permitting the first and second wires to be advanced and retracted with at least 1 cm of independence relative to each other. Also, a mesh tube having a distal and proximal end, is connected to the first wire and a blood-porous fragment guard is positioned at the distal end of the mesh tube. This fragment guard includes spokes joined at a central hub and extending radially and proximally from the central hub, and wherein the second wire is connected to the central hub so that when the second wire is pulled proximally relative to the first wire, the hub is pulled proximally, causing the spokes to spread out and causing the fragment guard to widen.

In addition to the exemplary aspects and embodiments described above, further aspects and embodiments will become apparent by reference to the drawings and by study of the following detailed descriptions.

BRIEF DESCRIPTION OF THE DRAWINGS

FIG. 1 is an isometric view of a stent retriever according to the present invention.

FIG. 2 is a sectional view of an artery clogged by a clot, with the stent retriever of FIG. 1 piercing the clot.

FIG. 3 is the sectional view of FIG. 2, with the stent retriever of FIG. 1 deployed.

FIG. 4 is the sectional view of FIG. 2, with the stent retriever of FIG. 1 further expanded and in the process of removing the clot.

Figure 5:
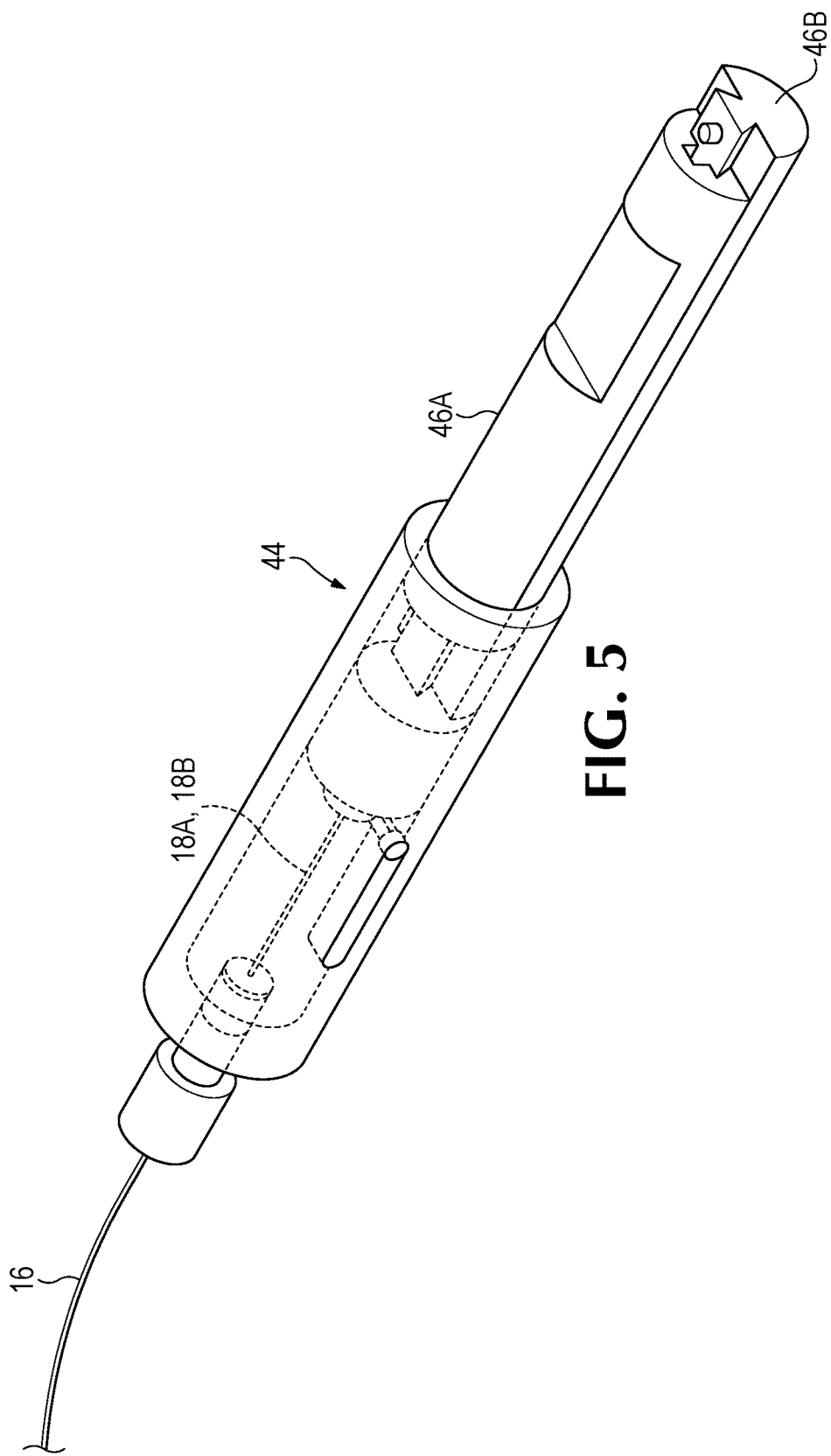
FIG. 5 is an isometric view of a catheter assembly, including a handle assembly, that could be used to control the stent retriever of FIGS. 1-4.

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Referring to FIGS. 1 and 2, In a preferred embodiment, a stent retriever 10 includes a wire mesh 12 and a woven fragment guard 14. it is controlled by a pair of wires 18A and 18B, which must be separately advanceable for the stent retriever 10 to work correctly. The stent retriever 10 is positioned in an artery 20, near a clot 22 by introduction of a catheter 16. After a distal end of catheter 16 is positioned near clot 22, the stent retriever 10 is deployed by pushing wires 18A and 18B forward. A system for permitting this action is shown and described in U.S. Pat. No. 8,876,863. After or during deployment the stent retriever 10 is pushed through clot 22, so that at least the fragment guard 14 is pushed all the way through.

Referring also to FIG. 3, wire 18B is advanced relative to wire 18A. Fragment guard 14 is made of a set of spokes 24 that meet in an apex 26, and are all covered by a fabric 28. When wire 18B is advanced, or wire 18A is retracted, then spokes 24 are spread apart (much as the spokes of an umbrella). The stent retriever is now pulled proximally, bringing the clot 22 with it, and with fragment guard 14 protecting the artery 20 further on in the direction of blood flow, from fragments that could break off from clot 22. Referring to FIG. 4, as the stent retriever 10 is pulled toward the incision where catheter 16 was introduced, artery 20 will typically widen. Wire 18A may be pulled further back relative to wire 18B, thereby widening out fragment guard 14. Wires 18B and 18A each support a radiopaque marker 40 and 42, respectively, to aid a surgeon in locating the stent retriever during a procedure. The two markers 40 and 42 are spaced apart and mutually distinguishable, to aid a surgeon in determining the orientation of stent retriever 10. In an alternative preferred embodiment, marker 42 is closer to the distal tip of retriever 10.

In one preferred embodiment, wire mesh 12 and spokes 24 are made of nitinol. In another preferred embodiment mesh 12 and spokes 24 are made of a titanium alloy. In one embodiment, fabric 28 is made of woven strands of expanded polytetrafluoroethylene (ePTFE). In one embodiment, the weave is loose, to permit blood to flow through the interstices of the threads. In still another embodiment, the fabric 28 is made of threads arranged in a circular manner about said spokes, to form a pattern similar to that of a spider web.

Referring to FIG. 5, catheter 16 is connected to a handle 44, having separately positionable positioners 46A and 46B, for wires 18A and 18B. Handle 44 permits a user to separately move wire 18A and 18B, for deployment and control of the fragment guard 14.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A stent retriever assembly having a proximal end and a distal end, and comprising:
    (a) a mesh tube having a distal and proximal end, and being connected to a first wire; and
    (b) a blood-porous fragment guard mounted at said distal end of said mesh tube, said fragment guard including spokes joined at a central hub and extending radially and proximally from said central hub, and wherein a second wire is connected to said central hub so that when said second wire is pulled proximally relative to said first wire, said hub is pulled proximally, causing said spokes to spread out and causing said fragment guard to widen, and wherein said first wire and said second wire are spaced apart laterally.

2. The stent retriever assembly of claim 1, wherein said mesh tube is made, at least in part, of a metal mesh that is stiff, so that when said second wire is pulled proximally, said metal mesh resists being pulled proximally, due to said stiffness.

3. The stent retriever assembly of claim 1, wherein said fragment guard, in addition to said spokes, includes threads extending across and between said spokes, to create a finer mesh, better able to hold clot material.

4. The stent retriever assembly of claim 1, wherein said mesh tube is collapsible, to be placed into a narrow state for penetrating through a clot.

5. The stent retriever assembly of claim 1, wherein when said second wire is pulled proximally relative to said first wire, said mesh tube expands outwardly with said fragment guard.

6. A method of removing a clot from an artery, comprising:
    (a) providing a stent retriever assembly having a proximal end and a distal end, and including:
        (i) a mesh tube having a distal and proximal end, and being connected to a first wire; and
        (ii) a blood-porous fragment guard mounted at said distal end of said mesh tube, said fragment guard including spokes joined at a central hub and extending radially and proximally from said central hub, and wherein a second wire is connected to said central hub so that when said second wire is pulled proximally relative to said first wire, said hub is pulled proximally, causing said spokes to spread out and causing said fragment guard to widen, and wherein said first wire and said second wire are spaced apart laterally;
    (b) deploying said stent retriever to a proximal side of said clot;
    (c) pushing said stent retriever through said clot;
    (d) pulling said second wire relative to said first wire, thereby widening said fragment guard; and
    (e) pulling said stent retriever proximally to pull material from said clot proximally.

7. The method of claim 6, wherein said blood clot is in a narrow artery, and wherein as said stent retriever is pulled proximally through said artery, said artery widens and said second wire is pulled further proximally relative to said first wire causing said fragment guard to widen further to more closely conform to the wider arterial walls.

8. The method of claim 6, wherein said blood clot is in a cranial artery.

9. The method of claim 6, wherein said stent retriever assembly includes a radiopaque element, and wherein during performance of the method location of said stent retriever assembly is monitored by means of said radiopaque element.

10. A stent retriever catheter assembly having a proximal end and a distal end, and comprising:
    (a) a catheter, including a flexible tube sized to fit through the arterial system of a person, and to reach a blood clot in an artery;
    (b) a first and second wire, extending through said tube;
    (c) a handle connected to said first and second wires, and wherein said first and second wires can be advanced and retracted with at least 1 cm of independence relative to each other,
    (d) a mesh tube having a distal and proximal end, and being connected at said proximal end to said first wire; and
    (e) a blood-porous fragment guard mounted at said distal end of said mesh tube, said fragment guard including spokes joined at a central hub and extending radially and proximally from said central hub, and wherein said second wire is connected to said central hub so that when said second wire is pulled proximally relative to said first wire, said hub is pulled proximally, causing said spokes to spread out and causing said fragment guard to widen, and wherein said first wire and said second wire are spaced apart laterally.

11. The stent retriever catheter assembly of claim 10, wherein said mesh tube is made, at least in part, of a metal mesh that is stiff, so that when said second wire is pulled proximally, said metal mesh resists being pulled proximally, due to said stiffness.

12. The stent retriever catheter assembly of claim 10, wherein said fragment guard, in addition to said spokes, includes threads extending across and between said spokes, to create a finer mesh, better able to hold clot material.

13. The stent retriever catheter assembly of claim 10, wherein said mesh tube is collapsible, to be placed into a narrow state for penetrating through a clot.

14. The stent retriever catheter assembly of claim 10, wherein when said second wire is pulled proximally relative to said first wire, said mesh tube expands outwardly with said fragment guard.

\* \* \* \* \*